United States Patent
González Bello et al.

(10) Patent No.: US 7,563,896 B2
(45) Date of Patent: Jul. 21, 2009

(54) PROCESS OF OBTAINING TYPE II DEHYDROQUINASE ENZYME INHIBITORS AND PRECURSORS THEREOF

(75) Inventors: Concepción González Bello, Santiago de Compostela (ES); Luis Castedo Expósito, Santiago de Compostela (ES)

(73) Assignee: Universidade de Santiago de Compostela, Santiago de Compostela (ES)

( * ) Notice: Subject to any disclaimer, the term of this patent is extended or adjusted under 35 U.S.C. 154(b) by 0 days.

(21) Appl. No.: 10/565,348

(22) PCT Filed: Jul. 16, 2004

(86) PCT No.: PCT/ES2004/000337

§ 371 (c)(1),
(2), (4) Date: Aug. 2, 2006

(87) PCT Pub. No.: WO2005/009330

PCT Pub. Date: Feb. 3, 2005

(65) Prior Publication Data

US 2007/0185214 A1     Aug. 9, 2007

(30) Foreign Application Priority Data

Jul. 21, 2003     (ES) .............................. 200301709

(51) Int. Cl.
 C07D 295/00    (2006.01)
 C07C 62/00    (2006.01)
(52) U.S. Cl. ....................... 544/403; 562/508
(58) Field of Classification Search ........ None
See application file for complete search history.

(56) References Cited

OTHER PUBLICATIONS

González-Bello, C. et al. "Parallel solid-phase synthesis and evaluation of inhibitors of Streptomyces coelicolor type II dehydroquinase" J. Med. Chem. 2003, vol. 46, No. 26, pp. 5735-5744.

Frederickson, M. et al. "Selective inhibition of type II dehydroquinase" J. Org. Chem. 1999, vol. 64, No. 8, pp. 2612-2613.

González-Bello, C. et al. "Synthesis of polyhydroxy cyclohexanes and relatives from (-)-quinic acid" J. Org. Chem. 2003, vol. 68, No. 6, pp. 2248-2255.

Montchamp, J.L. et al. "Cyclohexenyl and cyclohexylidene inhibitors of 3-dehydroquinate synthase: Active site interacions relevant to enzyme mechanism and inhibitor design" J. Am. Chem. Soc. 1997, vol. 119, No. 33, pp. 7645-7653.

Sutherland, J.K. et al. "The synthesis of 6α- and 6β-fluoroshikimic acids" J. Chem. Soc. Chem. Comm. 1989, vol. 18, pp. 1386-1387.

Harris, J.M. et al. "Comparison of the substrate specificity of type I and type II dehydroquinases with 5-deoxy- and 4,5-dideoxy-dehydroquinic acid" J. Chem. Soc., Perkin Trans. I 1996, vol. 19, pp. 2371-2377.

Carballido, M. et al. "Synthesis of carba-sugars from (-)-quinic acid" Tetrahedron Lett. 2002, vol. 42, pp. 3973-3976.

Phoon, C.W. "Use of quinic acid as template in solid-phase combinatorial synthesis" J. Comb. Chem. 1999, vol. 1, pp. 485-492.

*Primary Examiner*—Paul A Zucker
(74) *Attorney, Agent, or Firm*—Merchant & Gould P.C.

(57) ABSTRACT

The present invention relates to a process of obtaining type II dehydroquinase enzyme inhibitors and the precursors thereof from (−)-quinic acid. The described compounds have a carboxycyclohexene structure. The process of preparing the compounds and their application as compositions with pharmacological properties and herbicides of interest are described.

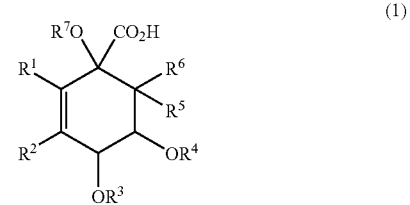

(1)

13 Claims, No Drawings

PROCESS OF OBTAINING TYPE II DEHYDROQUINASE ENZYME INHIBITORS AND PRECURSORS THEREOF

The present invention relates to the process of obtaining type II dehydroquinase enzyme inhibitors having a carboxycyclohexene structure, and to obtaining the intermediate precursors of said inhibitors. The compounds are prepared from (−)-quinic acid.

The inhibitors have the following formula:

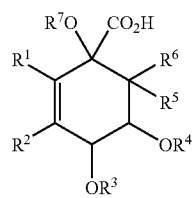

(1)

where $R^1$, $R^2$, $R^3$, $R^4$, $R^5$, $R^6$ and $R^7$ can be hydrogen, alkyloxy or alkyl with C1-C10 chains, or any aromatic group, or a benzyloxy group in which the aromatic ring can be substituted by one or several substituents chosen from halogen, nitro, guanidinium, azido, cyano, phosphate, amino, carboxy, amide, thiol, thioester, thioether, alcohol, alkoxy or alkyl groups with C1-C10 chains.

In the field of agriculture, the growth of undesirable weeds together with the crops creates significant problems, such as the decrease in production and quality, farm work and harvesting difficulties, and the need for manual labor or pesticides for their elimination. For this reason, unwanted weeds limit agricultural production and considerably affect their price. It is estimated that the decrease in production brought about by the growth of weeds is 15-20% the total crop value, mainly due to the competition of the weeds with the useful plants for the consumption of nutritive elements, water and light. As a result the use of herbicides has been imposed as one of the necessary operations for achieving stable, high-yield crops. The current treatment with herbicides is so extensive that it has given rise to a very important branch of the chemical industry.

It is necessary to discover new herbicides with maximum selectivity, such that they preferably attack weeds, minimally affecting the crops. Selectivity is often achieved by means of chemicals interfering in biogenetic pathways present in the weeds. Hence there are herbicides interfering in the biosynthesis of proteins, aromatic amino acids, lipids or carotenoids.

Chorismic acid is a key intermediate in the biosynthesis of the aromatic amino acids tyrosine, phenylalanine and tryptophan:

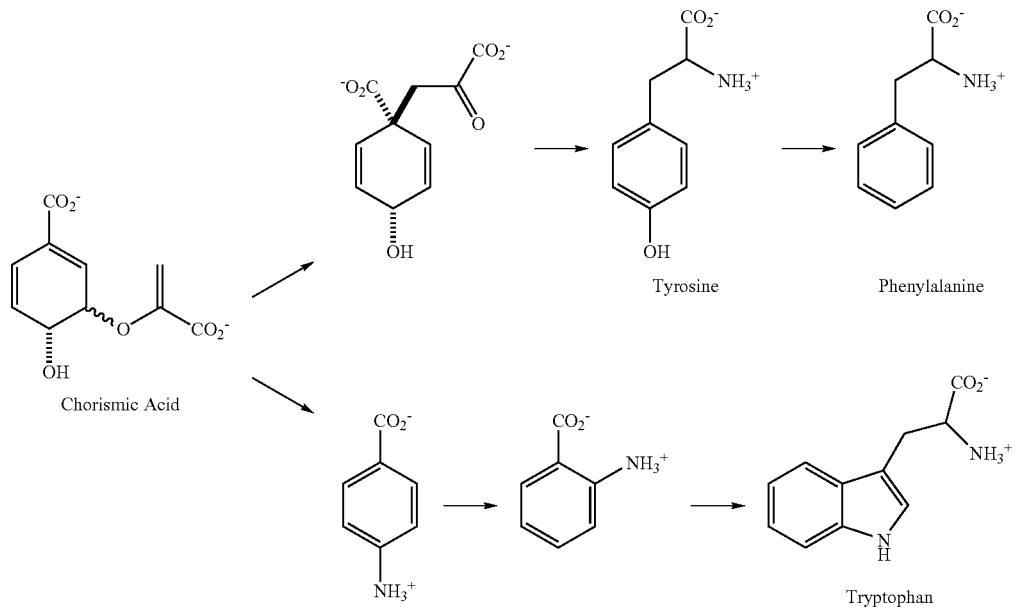

Chorismic acid is also a key intermediate in the biosynthesis of other biologically important products such as: p-aminobenzoate, folic acid, p-hydroxybenzoate and certain vitamins:

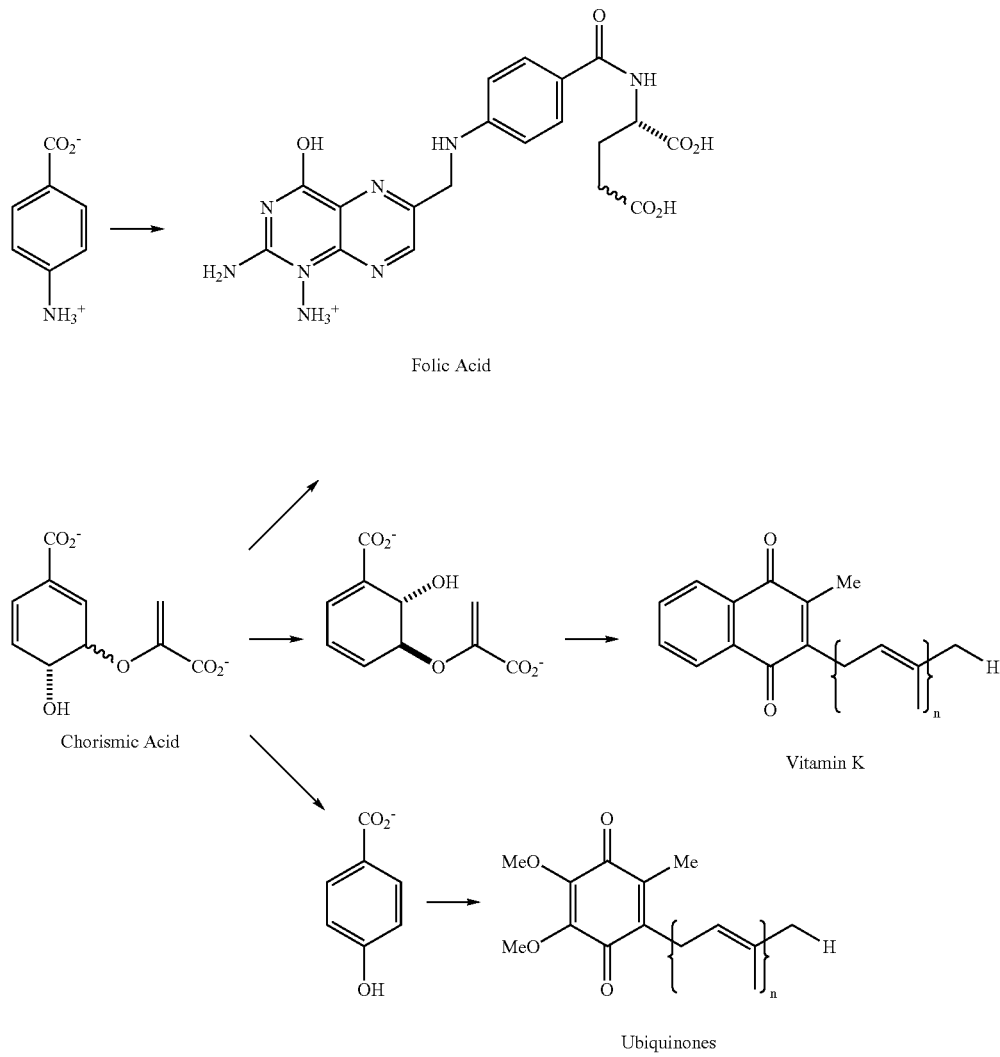

Folic Acid

Chorismic Acid

Vitamin K

Ubiquinones

Chorismic acid is in turn biosynthesized by means of a series of chemical reactions known with the name of the shikimic acid pathway (for a review on this topic please see (a) Abell, C. *Enzymology and Molecular Biology of the Shikimate Pathway: Comprehensive Natural Products Chemistry*, Sankawa, U.; Pergamon, Elsevier Science Ltd. Oxford, 1999, Vol 1, page 573; (b) Haslam, E. *Shikimic Acid: Metabolism and Metabolites*, John Wiley, Chichester, 1993). This biosynthetic pathway is present in the secondary metabolism of plants, fungi and bacteria, but not in animals (Hawkins, A. R. *CRC Crit. Rev. Biochem.* 1990, 25, 307), so it is considered a very important source for the development of new herbicides, fungicides or antibiotics capable of selectively blocking certain enzymatic transformations of this biosynthetic pathway (please see: (1) Jaworski, E. G. *Food Chem.* 1972, 20, 1195. (b) Baillie, A. C.; Corbett, J. R.; Dowsett, J. R.; McCloskey, P. *Pestic. Sci.* 1972, 3, 113. (c) Kishore, G. M.; Shah, D. M. *Annun. Rev. Biochem.* 1988, 57, 627). It must be taken into account that an herbicide acting on a metabolic pathway present in plants but not in animals is expected to present minimum toxicity in humans. The best herbicide currently produced world-wide, Glyphosphate, acts precisely by inhibiting the sixth enzyme of the shikimic acid pathway (EPSP synthase) with a magnificent inhibition constant of about 1 μM (please see: (a) Steinrucken, H. C.; Amerhein, N. *Eur. J. Biochem.* 1984, 143,351. (b) Steinrucken, H. C.; Amerhein, N. *Biochem. Biophys. Res. Commun.* 1980, 94, 1207). Glyphosphate forms a complex with the enzyme and 3-phosphate shikimate which inhibits enzymatic activity and is considered to be responsible for the herbicidal activity thereof. Glyphosphate is the active component of the Roundup and Tumbleweed herbicides widely used as selective, post-emergent low toxicity herbicides.

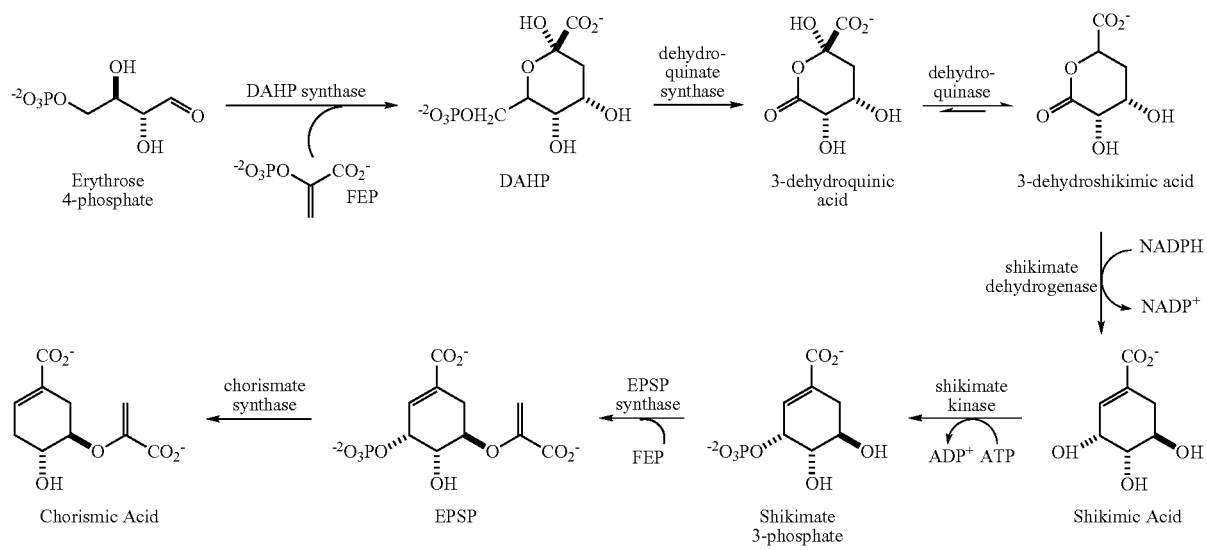

It must be further stressed that recently Roberts et al. (*Nature* 1998, 393, 801) demonstrated the surprising presence of these enzymes of the shikimic acid pathway in certain animal parasites of the *Phylum apicomplexa*, such as the *Toxoplasma gondii, Plasmodium falciparum* (malaria) and *Cryptosporidium parvum*. Therefore herbicides inhibiting the shikimic acid pathway may be effective against these organisms. In fact, it has been proven that glyphosphate is effective against malaria (see: (a) McFadden, G. I.; Keith, M. E.; Monholland, J. M.; Lang-Unasch, N. *Nature* 1996, 381, 482; (b) Fichera, M. E.; Roos, D. S. *Nature* 1997, 390, 407). This disease together with AIDS and tuberculosis, form the most deadly trio of infectious diseases for mankind as of today according to the World Health Organization. Therefore it is possible that compounds with herbicidal properties may additionally have antimalarial activity.

It is therefore possible to obtain compounds with a broad activity spectrum. The considerable interest in them is based on the fact that they can be used in the treatment of diseases caused by several pathogenic agents simultaneously infecting a living being.

A selective and effective herbicide inhibiting some of the enzymes present in the shikimic acid pathway can be obtained. The interest of the inventors is focused on the third enzyme of this biosynthetic pathway, dehydroquinase (3-dehydroquinate dehydratase, EC 4.2.1.10), which catalyzes 3-dehydroquinic acid dehydration to 3-dehydroshikimic acid. Two types of dehydroquinases, referred to as type I and type II, are known due to their different biophysical properties and the different amino acid sequence they have (see Hawkins, A. R. *Curr. Genet.* 1987, 11, 491). Both types catalyze the same transformation but by means of different mechanisms and with opposite stereochemistry (see Kleanthous, C.; Davis, K.; Kelly, S. M.; Cooper, A.; Harding, S. E.; Price, N. C.; Hawkins, A. R.; Coggins, J. R. *Biochem. J.* 1992, 282, 687). Type II dehydroquinases, which come from different sources (*Mycobacterium tuberculosis, Streptomyces coelicolor* and *Aspergillus nidulans*) are dodecameric (12-16 KDa) and thermally stable, whereas the type I enzymes are dimeric (27 KDa) and temperature-sensitive.

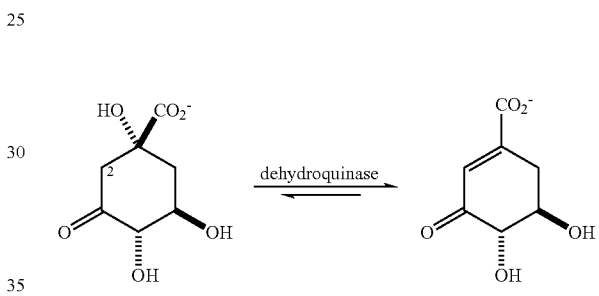

The most studied enzyme is dehydroquinase type I, from *Escherichia coli* (see Chauduri, C.; Ducan, K.; Graham, L. D.; Coggins, J. R. *Biochem. J.* 1990, 275, 1). Coggins et al. (*J. Am. Chem. Soc.* 1991, 113, 9416; *J. Biol. Chem.* 1995, 270, 25827) proved that its mechanism of action occurs through the formation of a Schiff base between the ketone group and a lysine residue in the active center (Lys170). This entails the loss of the pro-R hydrogen at C-2, globally corresponding to an elimination of water in syn (see: (a) Hanson, K. R.; Rose, I. A. *Proc. Natl. Acad. Sci. USA* 1963, 50, 981; (b) Smith, B. W.; Turner, M. J.; Haslam, E. *J. Chem. Soc., Chem. Commun.* 1970, 842; (c) Haslam, E.; Turner, M. J.; Sargent, D.; Thompson, R. S. *J. Chem. Soc. (C)* 1971, 1489).

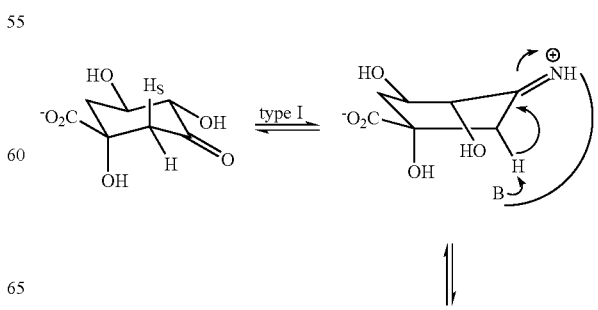

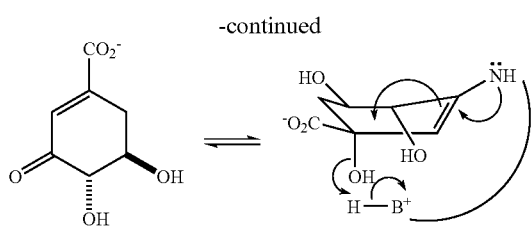

In contrast, the type II enzyme (see: (a) Gourley, D. G.; Coggins, J. R.; Isaacs, N. W.; Moore, J. D.; Charles, I. G.; Hawkins, A. R. *J. Mol. Biol.* 1994, 241, 488; (b) Krell, T.; Pilt, A. R.; Coggins, J. R. *FEBS Lett.* 1995, 360, 93) catalyzes the elimination of water in anti with the loss of the hydrogen plus acid, the pro-S (see: (a) Shneier, A.; Harris, J.; Kleanthous, C.; Coggins, J. R.; Hawkins, A. R.; Abell, C. *Bioorg. Med. Chem. Lett.* 1993, 3, 1399; (b) Harris, J.; Kleanthous, C.; Coggins J. R.; Hawkins, A. R.; Abell, C. *J. Chem. Soc., Chem. Commun.* 1993, 13, 1080). Abell et al. proposed that the reaction occurs through an E1CB mechanism through an intermediate enolate (*Biochem. J.* 1996, 319, 333).

Recently, Lapthorn et al. (*Structure* 2002, 10, 493) were able to resolve the crystalline structure of the type II dehydroquinase from *Streptomyces coelicolor*. This X-ray structure has allowed clearly defining both the position and the structure of the active center. And more importantly it has clarified the role that the amino acids of the active center play as well as confirmed the enolic mechanism previously proposed by Abell.

Lapthorn et al. propose that Tyr28 acts as a base in the first step of abstraction of the axial proton at alpha to the ketone. It must be pointed out that this Tyr residue is deprotonated due to the basic environment in which it is located and which Arg113 is responsible for. After deprotonation, they propose that the substrate forms an enolate intermediate. And although there is no residue that is close enough to stabilize the negative charge, a water molecule is correctly located in its place at 2.8 Å from this group coordinated with the amide group of Asn16, the carbonyl of Pro15 and the nitrogen of Ala82. The elimination of water finally occurs, which step is catalyzed by His106 acting as a proton donor, and the carbonyl of Asn79 also acting as a proton accepter, favoring the final elimination of water.

A class of compounds is described in the present invention that is characterized by having a six-membered ring with a double bond between positions 5 and 6 and a carboxylic group at position 1. Objectives of this invention are compounds with the hereinbefore mentioned basic structure in which the $R^1$, $R^2$, $R^3$, $R^4$, $R^5$, $R^6$ and $R^7$ groups can be hydrogen, alkyloxy, alkyl with C1-C10 chains, or any aromatic group, or a benzyloxy group in which the aromatic ring may be substituted by one or several identical or different radicals, chosen from halogen, polyhalogenated alkyl, nitro, azido, amino, phosphate, carboxy, amide, thiol, thioester, guanidinium, thioether, alcohol, alkoxy or alkyl groups with C1-C10 chains.

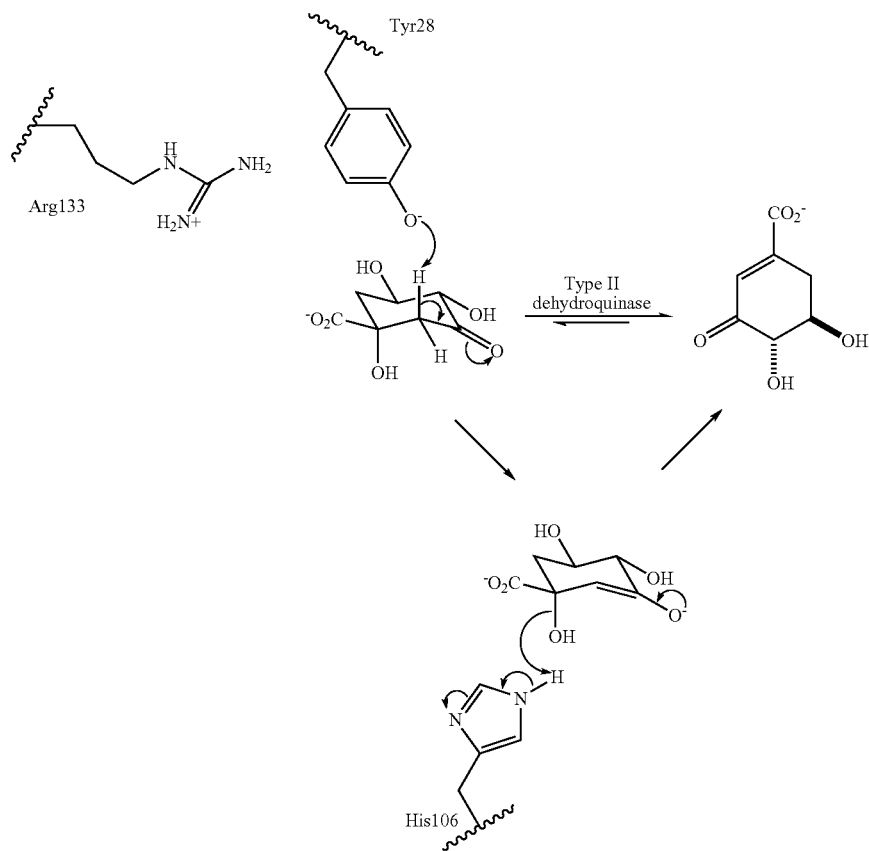

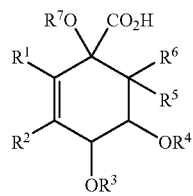

In all of them, the different substituents are radicals of the following type: linear or branched alkyl with 1-10 carbon atoms, alkenyl with 2 to 10 carbon atoms, alkynyl with 3 to 10 carbon atoms, cycloalkyl with 3 to 6 carbon atoms, cycloalkenyl with 4 to 6 carbon atoms, or bicycloalkyl with 7 to 10 carbon atoms; these radicals possibly being substituted by one or several identical or different substituents chosen from halogen atoms and the hydroxy, amino, thiol, azido, nitro, phosphate and alkoxy radicals containing 1 to 4 carbon atoms, piperidinyl, morpholinyl, indole, furan, piperazinyl-1 (possibly substituted at –4 by an alkyl radical with 1 to 4 carbon atoms or by a phenylalkyl radical, the alkyl part of which contains from 1 to 4 carbon atoms), cycloalkyl with 3 to 6 carbon atoms, cycloalkenyl with 4 to 6 carbon atoms, phenyl, cyano, nitro, carboxy, alkoxycarbonyl, halogen, amino or amide, the alkyl part of which contains 1 to 4 carbon atoms, or a phenyl radical, possibly substituted by one or several identical or different radicals, chosen from the alkyl radicals with 1 to 4 carbon atoms, halogenated or not, or an alkoxy with 1 to 4 carbon atoms, or halogen, nitro, azido, phosphate, amino, cyano, amide, thiol, thioester, guanidinium, thioether or alcohol groups, a saturated or unsaturated nitrogenous heterocyclic radical containing 1 to 4 carbon atoms, a saturated or unsaturated nitrogenous heterocyclic radical containing 5 or 6 members, possibly substituted by one or several alkyl radicals with 1 to 4 carbon atoms, understanding that the cycloalkyl, cycloalkenyl or bicycloalkyl radicals can possibly be substituted by one or several alky radicals containing 1 to 4 carbon atoms.

Also object of the present invention are the herbicidal and pharmaceutical properties of the compounds hereinbefore mentioned, including their anticancerous and antibiotic properties. The process of obtaining said compounds is finally described.

The process of obtaining these compounds is based on the chemical modification by means of simple transformations of a basic skeleton, either by means of solution chemistry or by means of solid support chemistry. The key steps of these transformations consist of the alkylation of the alkoxides derived from these basic compounds, suitably functionalized, either in a solution or a solid support with different electrophiles; the cleaving of the compounds from the resin for the case of solid support synthesis, and finally the hydrolysis reaction leading to obtaining the acid group.

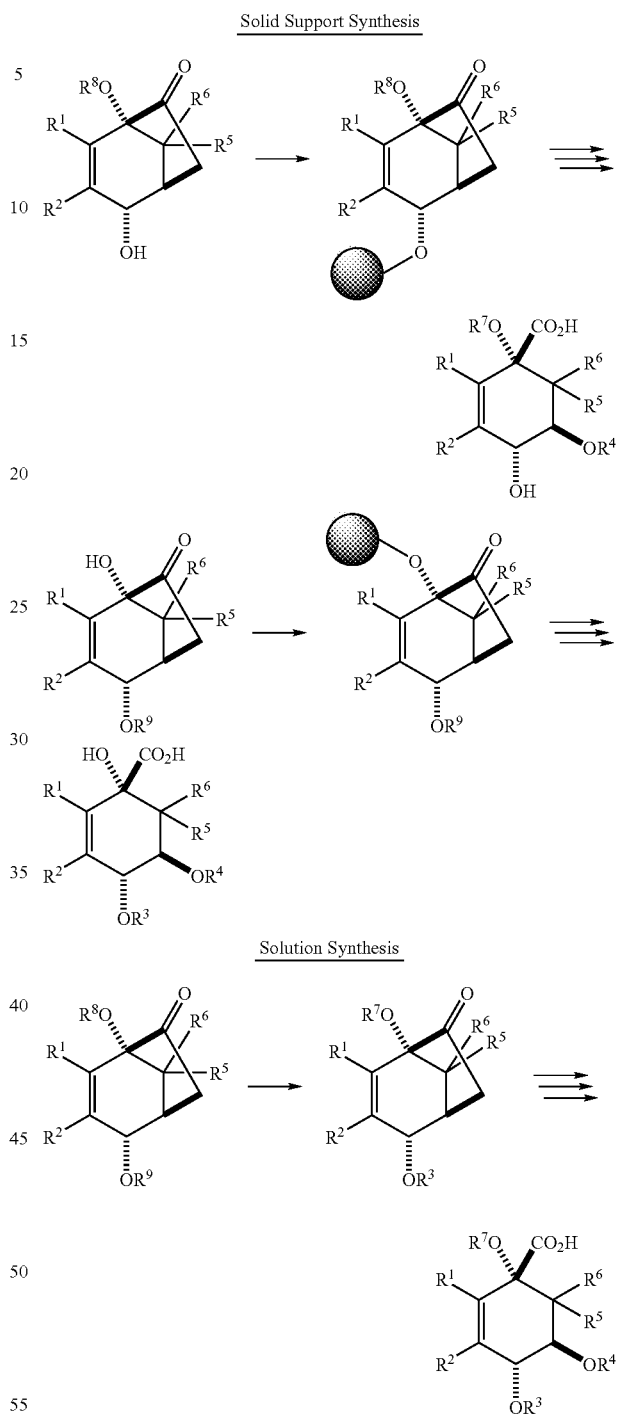

EXAMPLE 1

The cyclohexene acids (VI) were prepared following the mentioned solid phase synthetic strategy and using carbolactone I, BromoWang polystyrene resin and the corresponding benzyl bromide derivative as starting materials.

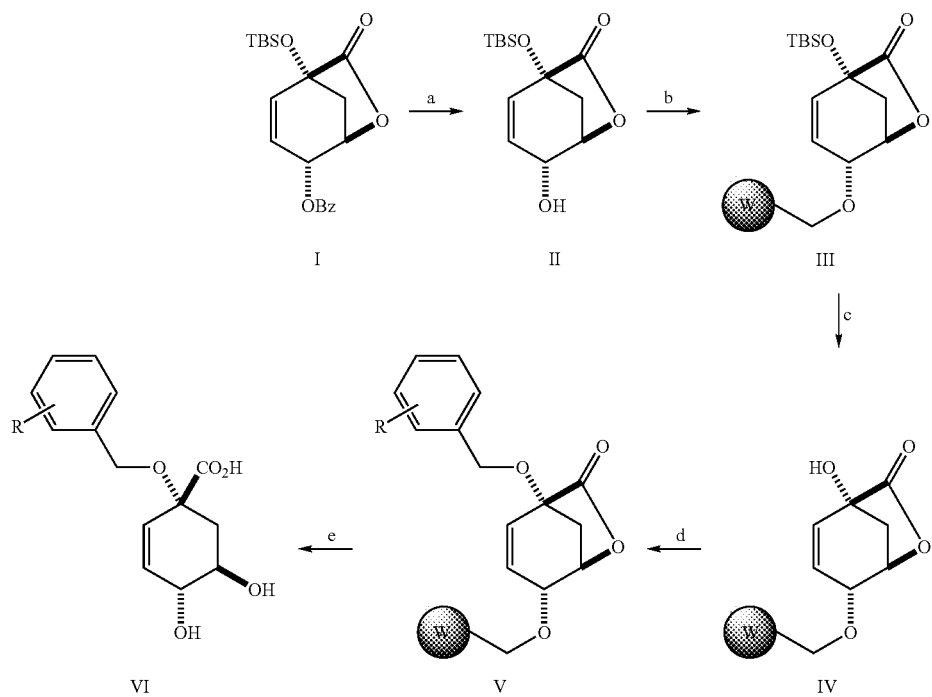

(a) $K_2CO_3$, MeOH, 60° C., 67%; (b) 1. HNa, DMF, 0° C.; 2. BromoWang resin, 15-crown-5, r.t.; (c) TBAF, THF, r.t.; (d) 1. HNa, DMF, 0° C.; 2. R-phenyl-$CH_2$Br, 15-crown-5, 40-80° C.; (e) 1. 50% TFA/DCM, 2. LiOH, THF, r.t., 3. Amberlite IR-120 ($H^+$).

Therefore, treatment of carbolactone I with potassium carbonate in methanol provides allyl alcohol II (see González, C.; Carballido, M.; Castedo, L. *J. Org. Chem.* 2003, 68, 2248) which, by means of treating with sodium hydride and subsequent reaction with BromoWang polystyrene resin leads to ether III. Treatment of the ether III with tetrabutylammonium fluoride provides the tertiary alcohol IV which, by reaction with sodium hydride and subsequent reaction with the corresponding benzyl bromides gives rise to ethers V. The desired acids V are finally obtained by means of a three-step process first consisting of breaking the bond with the resin by reaction with trifluoroacetic acid, basic hydrolysis of the lactone and finally treatment with Amberlite IR-120, an ion exchange resin.

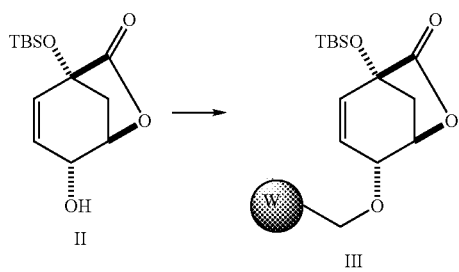

Preparation of Resin III. Sodium hydride (222 mg, 5.54 mmol, 60% commercial suspension in mineral oil) was added to a solution of alcohol II (1.4 g, 5.18 mmol) in dry DMF (20 mL) cooled at 0° C. and under an argon atmosphere. After 30 minutes at said temperature, the resulting suspension was added by means of a cannula to a suspension of the BromoWang polystyrene resin (1 g, ~1.6 mmol/g) in dry DMF (17 mL) cooled at 0° C. and under an argon atmosphere. Then 15-crown-5 ether (30 μL, 0.26 mmol) was added and the resulting suspension was gently stirred at 0° C. for 30 minutes and at room temperature for 24 hours. The resin was filtered and successively washed with DMF (3×15 mL), (3:1) DMF/water (3×15 mL), THF (3×15 mL) and dichloromethane (3×15 mL). 1.02 g of resin III were obtained in a pale yellow granule form after vacuum-drying. IR (gel/$cm^{-1}$) 1797 and 1611; $^{13}$C-NMR (gel, 63 MHz, $CDCL_3$, δ) 128.5, 118.7, 114.7, 73.7, 71.2, 69.9, 64.8, 40.0, 37.7, 25.6 and −3.1.

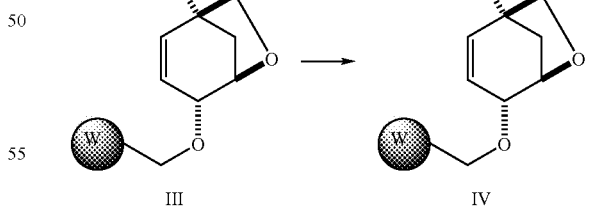

Preparation of Resin IV. Tetrabutylammonium fluoride (1.4 mL, 1M commercial solution in THF) was added to a suspension of resin III (1 g, ~1 mmol) in dry THF (16 mL) at 0° C. and under inert atmosphere. The resulting suspension was gently stirred for 2 hours at room temperature. The resin was filtered and washed successively with THF (3×15 mL), (3:1) 5% HCl/THF (3×15 mL), THF (3×15 mL) and dichloromethane (3×15 mL). 0.9 g of resin IV were obtained in the form of pale yellow grains after vacuum-drying. IR (gel/cm$^{-1}$) 3414, 1789 and 1609; $^{13}$C-NMR (gel, 63 MHz, CDCL$_3$, δ) 136.4, 129.5, 121.5, 115.3, 74.6, 71.1, 53.5 and 36.9.

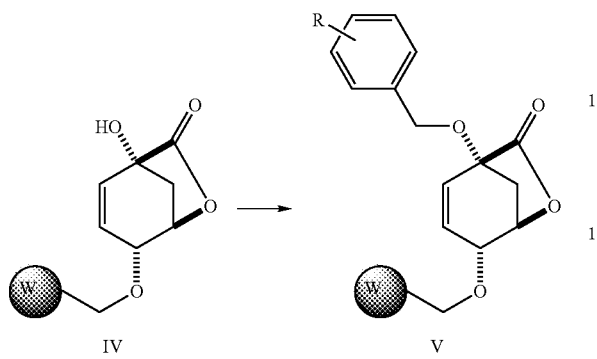

General Alkylation Process. A suspension of resin IV in dry DMF (1 mL for every 100 mg of resin) at 0° C. and under inert atmosphere was treated with 6 equivalents of sodium hydride (60% commercial suspension in mineral oil). The resulting suspension was gently stirred for 1 hour at room temperature and then 10 equivalents of the corresponding benzyl bromide and 0.3 equivalents of 15-crown-5 ether were added. The resulting suspension was heated between 40-80° C. for 24 to 48 hours. The resin was filtered and washed with THF (3×), (3:1) 10% HCl/THF (3×) and dry dichloromethane (3×) to give rise to resin V.

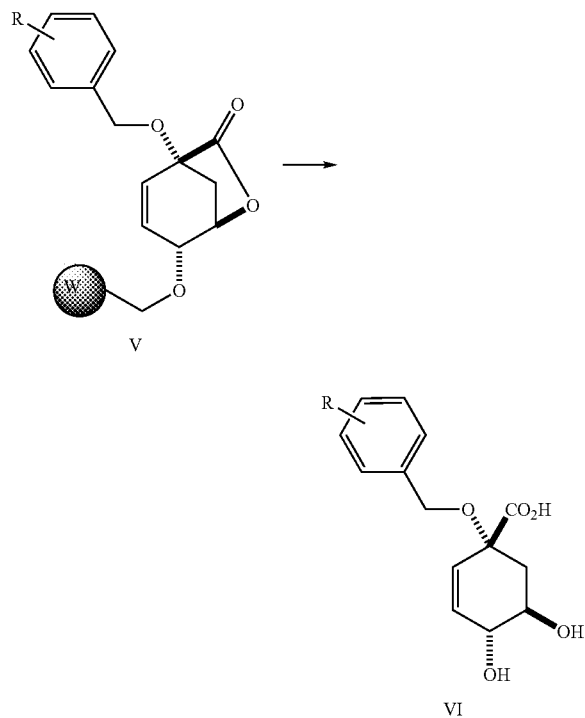

General Process of Breaking the Resin Compounds. The resin was treated at room temperature for 1 hour with a 50% TFA/dichloromethane mixture (1 mL for every 100 mg of resin). The resin was filtered and washed with dichloromethane (3×). The filtrate was concentrated under reduced pressure and vacuum-dried for 15 minutes. The obtained residue was redissolved in THF and treated with 5 equivalents of a 0.5 M lithium hydroxide aqueous solution. After 30 minutes, milliQ water was added and the aqueous phase was washed with diethyl ether (3×). The aqueous extract was treated with Amberlite IR-120 (H$^+$) to pH 6. The resin was filtered and washed with milliQ water. The filtrate was lyophilized so as to yield a colorless oil or foam, as appropriate.

The data of some compounds obtained using this process is given below:

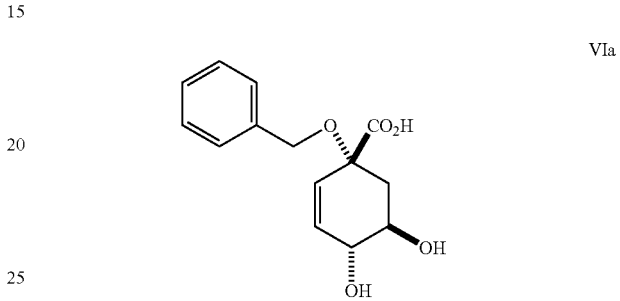

(1R,3R,4R)-1-benzyloxy-3,4-dihydroxycyclohex-5-ene-1-carboxylic acid (VIa). $[\alpha]^{25}_D$+15° (c 0.7 in H$_2$O); $^1$H-NMR (250 MHz, D$_2$O, δ) 7.31 (m, 5H), 5.93 (d, 1H, J 10.1), 5.82 (dd, 1H, J 10.1 and 1.8), 4.41 (s, 2H), 4.00 (dd, 1H, J 8.3 and 1.8), 3.77 (td, 1H, J 8.3, 11.9 and 3.5), 2.14 (dd, 1H, J 13.6 and 3.5) and 1.87 (t, 1H, J 13.6 and 11.9); $^{13}$C-NMR (100 MHz, D$_2$O, δ) 178.1, 137.9, 134.2, 128.8, 128.8, 128.4, 127.3, 80.8, 72.6, 69.5, 67.7 and 37.9; IR (KBr)/cm$^{-1}$ 3434, 1714 and 1578; EM-IQ$^+$ (m/z) 247 (MH$^+$—H$_2$O); HRMS calculated for C$_{14}$H$_{15}$O$_4$ (MH$^+$): 247.0970, 247.0965 found.

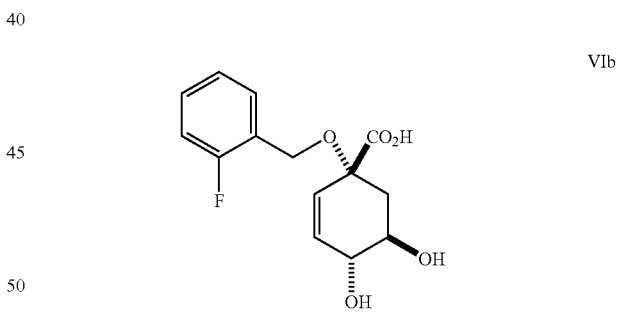

(1R,3R,4R)-1-(2'-fluorobenzyloxy)-3,4-dihydroxycyclohex-5-ene-1-carboxylic acid (VIb). $[\alpha]^{25}_D$-5° (c 0.7 in H$_2$O); $^{19}$F-NMR (282 MHz, D$_2$O, δ) −117.0 (dt, 1F, J 10.5 and 6.3); $^1$H-NMR (250 MHz, D$_2$O, δ) 7.41-7.29 (m, 2H), 7.15-7.02 (m, 2H), 5.94 (d, 1H, J 10.1), 5.86 (dd, 1H, J 10.1 and 1.7), 4.50 (s, 2H), 4.02 (dt, 1H, J 8.2 and 1.7), 3.78 (ddd, 1H, J 12.1, 3.6 and 8.2), 2.18 (ddd, 1H, J 13.7, 3.6 and 1.4) and 1.90 (dd, 1H, J 13.7 and 12.1); $^{13}$C-NMR (63 MHz, D$_2$O, δ) 177.8, 161.2 (J 244), 135.0, 131.8 (J 4), 130.9 (J 8), 127.0, 124.6 (J 18), 124.7, 115.7 (J 21), 80.3, 72.7, 69.6, 61.6 (J 4) and 37.8 (CH$_2$); IR (KBr)/cm$^{-1}$ 3420, 1717 and 1589; EM-IQ$^+$ (m/z) 265 (MH$^+$—H$_2$O); HRMS calculated for C$_{14}$H$_{14}$O$_4$F (MH$^+$): 265.0876, 265.0876 found.

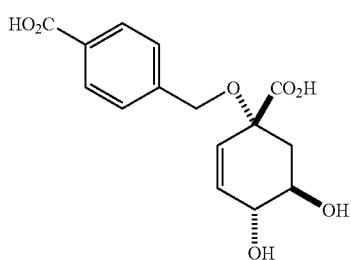

VIc (1R,3R,4R)-3,4-dihydroxy-1-(4'-carboxy)benzyloxycyclohex-5-ene-1-carboxylic acid (VIc). M.P. 161-162° C.; $[\alpha]^{25}_D$+16° (c 1.3 in $CH_3OH$); $^1$H-NMR (250 MHz, $CD_3OD$, δ) 7.94 (d, 2H, J 8.2), 7.45 (d, 2H, J 8.2), 6.01 (d, 1H, J 10.1), 5.87 (dd, 1H, J 10.1 and 1.9), 4.61 (d, 1H, J 11.8), 4.54 (d, 1H, J 11.8), 3.99-3.82 (m, 2H), 2.26 (dd, 1H, J 13.2 and 3.4), and 1.96 (dd, 1H, J 13.2 and 11.5); $^{13}$C-NMR (63 MHz, $CD_3OD$, δ) 177.0, 170.0, 145.6, 135.7, 130.6, 128.5, 128.2, 80.7, 74.1, 70.9, 67.5 and 30.8; IR (KBr)/cm$^{-1}$ 3444 and 1697; EM-IQ$^+$ (m/z) 291 (MH$^+$—$H_2O$); HRMS calculated for $C_{15}H_{15}O_6$ (MH$^+$): 291.0869, 291.0873 found.

EXAMPLE 2

Cyclohexene acid (IX) was prepared following the mentioned synthetic strategy in solution, using hydroxycarbolactone II and 4-nitrobenzyl bromide as starting materials. Thus, treatment of the sodium alkoxide derivative of hydroxylactone II with 4-nitrobenzyl bromide provides ether VII which, by reaction with tetrabutylammonium fluoride, gives the tertiary alcohol VIII. Finally, the basic hydrolysis of lactone VIII and subsequent treatment with the ion exchange resin Amberlite IR-120 provides the desired compound IX.

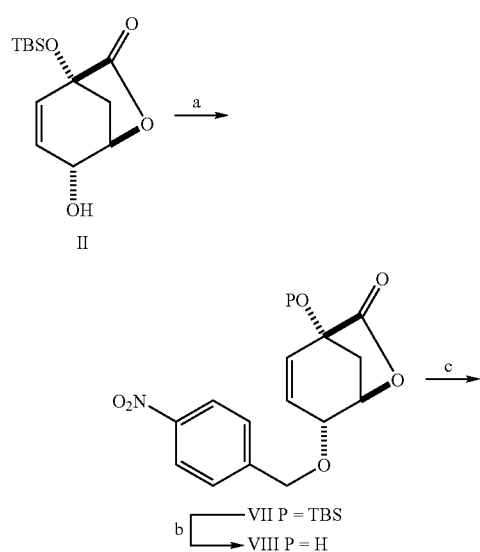

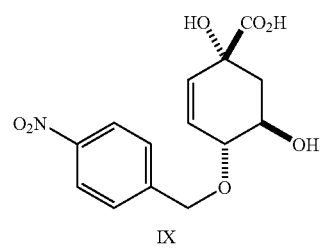

IX (a) 1. HNa, DMF, 0° C.; 2. 4-nitrobenzyl bromide, Bu$_4$NI, 15-crown-5, 80° C.; (b) TBAF, THF, 0° C.; (c) 1. LiOH, THF, r.t., 2. Amberlite IR-120 (H$^+$).

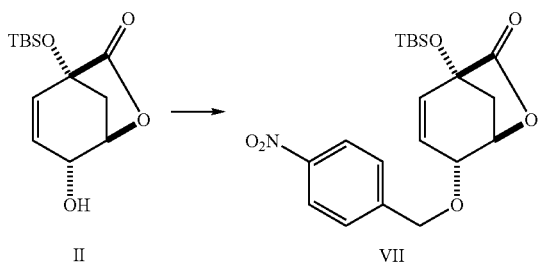

Preparation of (1R,3R,4R)-1-(tert-butyldimethylsilyloxy)-4-(4'-nitrobenzyloxy)cyclohex-5-ene-1,3-carbolactone (VII). Sodium hydride (29 mg, 0.73 mmol, 60% commercial suspension in mineral oil) was added to a solution of alcohol II (164 mg, 0.61 mmol) in dry DMF (6 mL) at 0° C. and under an argon atmosphere. After 30 minutes at this temperature, 4-nitrobenzyl bromide (171 mg, 0.79 mmol), tetrabutylammonium iodide (23 mg, 0.06 mmol) and 15-crown-5 ether (10 μL, 0.08 mmol) were added. The resulting blue solution was heated at 80° C. for 48 hours. The obtained suspension was diluted with diethyl ether (5 mL) and with water (15 mL). The organic phase was separated and the aqueous phase extracted with diethyl ether (3×20 mL). The pooled organic phase was dried (Na$_2$SO$_4$ anh.), filtered and concentrated under reduced pressure. The obtained residue was purified by means of flash chromatography in silica gel (70% dichloromethane/hexanes) to give 60 mg (24%) of ether VII in a pale yellow solid form. $[\alpha]^{25}_D$−172° (c 2.0 in CHCl$_3$); $^1$H-NMR (250 MHz, CDCl$_3$, δ) 8.21 (d, 2H, J 8.8), 7.50 (d, 2H, J 8.8), 6.15 (ddd, 1H, J 9.8, 1.7 and 1.0), 5.78 (ddd, 1H, J 9.8, 3.2 and 1.1), 4.77 (s, 2H), 4.73 (m, 1H), 3.98 (t, 1H, J 3.2), 2.42 (ddd, 1H, J 10.6, 5.2 and 1.8), 2.37 (d, 1H, J 10.6), 0.90 (s, 9H), 0.17 (s, 3H) and 0.14 (s, 3H); $^{13}$C-NMR (63 MHz, CDCl$_3$, δ) 175.3, 147.5, 144.9, 138.9, 127.7, 124.2, 123.7, 75.0, 73.4, 72.4, 70.9, 37.7, 25.5, 17.9 and −3.1; IR (NaCl)/cm$^{-1}$ 1793; EM-IQ$^+$ (m/z) 406 (MH$^+$); HRMS calculated for $C_{20}H_{28}O_6$NSi (MH$^+$): 406.1686, 406.1676 found.

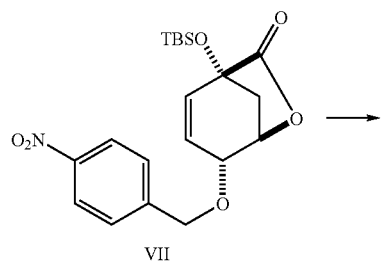

VII

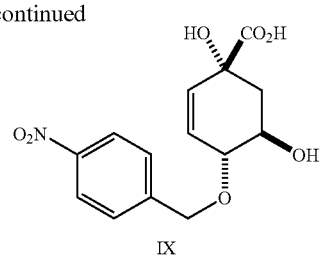

IX

Preparation of (1R,3R,4R)-1,3-dihydroxy-4-(4'-nitrobenzyloxy)cyclohex-5-ene-1-carboxylic acid (IX). A solution of carbolactone VIII (28 mg, 0.10 mmol) in 1 mL of THF and 0.5 mL of a 0.5 M lithium hydroxide aqueous solution was stirred at room temperature for 1 hour. The resulting solution was diluted with milliQ water (5 mL) and treated with Amberlite IR-120 (H$^+$) to pH 6. The resin was filtered and washed with milliQ water (15 mL). The filtrate was concentrated under reduced pressure to give 23 mg of acid IX (74%) in a pale solid yellow form. $[\alpha]^{25}_D$ –121° (c 1.1 in CH$_3$OH); $^1$H-NMR (250 MHz, CD$_3$OD, δ) 8.20 (d, 2H, J 8.8), 7.65 (d, 2H, J 8.8), 5.93 (dd, 1H, J 10.0 and 1.8), 5.73 (d, 1H, J 10.0), 4.84 (s, 2H), 4.04 (m, 1H), 3.93 (dt, 1H, J 7.9 and 1.8) and 2.07 (m, 2H); $^{13}$C-NMR (63 MHz, CD$_3$OD, δ) 176.8, 147.6, 147.1, 130.4, 129.3, 128.1, 123.4, 81.1, 73.5, 70.4, 68.2 and 40.2; IR (KBr)/cm$^{-1}$ 3528 and 1596; EM-IQ$^+$ (m/z) 310 (MH$^+$); HRMS calculated for C$_{14}$H$_{16}$NO$_7$ (MH$^+$): 310.0928, 310.0928 found.

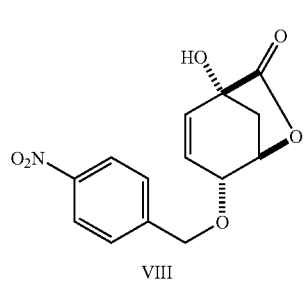

VIII

Preparation of (1R,3R,4R)-1-hydroxy-4-(4'-nitrobenzyloxy)cyclohex-5-ene-1,3-carbolactone (VIII). Tetrabutylammonium fluoride (0.25 mL, 0.25 mmol, 1.0 M commercial solution in THF) was added to a solution of silyl ether VII (95 mg, 0.23 mmol) in 2 mL of dry THF under an argon atmosphere and at 0° C. After stirring for 30 minutes at said temperature, it was acidulated with 10% HCl and the organic phase was extracted with dichloromethane (3×15 mL). The pooled organic phase was dried (Na$_2$SO$_4$ anh.), filtered and concentrated under reduced pressure. The obtained residue was purified by means of flash chromatography in silica gel (diethyl ether) to give 29 mg of alcohol VIII in a pale yellow oil form (43%). $[\alpha]^{25}_D$ –265.5° (c 1.2 in CHCl$_3$); $^1$H-NMR (250 MHz, CDCl$_3$, δ) 8.22 (d, 2H, J 8.7), 7.51 (d, 2H, J 8.7), 6.17 (d, 1H, J 9.8), 5.82 (ddd, 1H, J 9.8, 3.3 and 1.0), 4.81 (m, 1H), 4.78 (s, 2H), 4.02 (t, 1H, J 3.3), 3.35 (broad s, 1H) and 2.44 (m, 2H); $^{13}$C-NMR (63 MHz, CDCl$_3$, δ) 177.2, 147.6, 144.8, 137.4, 127.7, 125.1, 123.8, 74.5, 73.4, 72.2, 71.0 and 36.9; IR (NaCl)/cm$^{-1}$ 3405 and 1784; EM-IQ$^+$ (m/z) 292 (MH$^+$); HRMS calculated for C$_{14}$H$_{14}$O$_6$N (MH$^+$): 292.0821, 292.0826 found.

EXAMPLE 3

Cyclohexene acids (XIV) were prepared following the second solid phase synthetic strategy and using carbolactone X, BromoWang polystyrene resin and the corresponding benzyl bromide derivative as starting materials. Thus, treatment of carbolactone I with tetrabutylammonium fluoride provides alcohol X which, by treatment with sodium hydride and subsequent reaction with the BromoWang polystyrene resin leads to ether XI. Deprotection of the benzoyl group is carried out by means of treatment of ether XI with potassium cyanide and gives resin XII in carbolactone XIIa form and methyl ester XIIb form. Treatment of the resin XII with sodium hydride and subsequent reaction with the corresponding benzyl bromides gives ethers XIII. Finally, the desired acids XIV are obtained by means of a three-step process consisting first of breaking the bond with the resin by means of treatment with trifluoroacetic acid, basic hydrolysis of the lactone and finally treatment with an ion exchange resin, Amberlite IR-120.

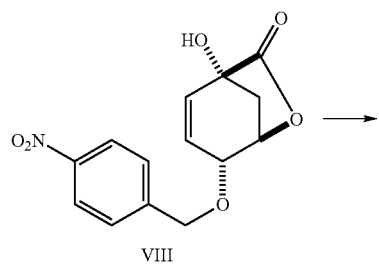

VIII

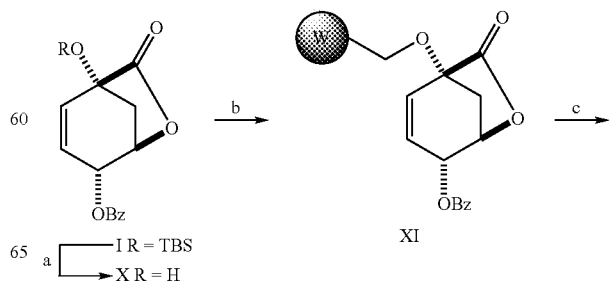

a ⌈ I R = TBS
  ⌊→ X R = H

XI

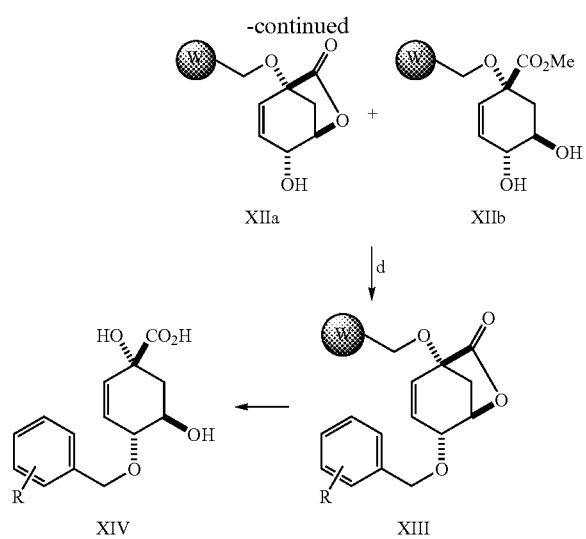

(a) TBAF, THF, 0° C.; (b) 1. HNa, DMF, 0° C.; 2. BromoWang resin, Bu₄NI, 15-crown-5, 80° C.; (c) KCN, MeOH, r.t.; (d) 1. HNa, DMF, 0° C.; 2. R-phenyl-CH₂Br, Bu₄NI, 15-crown-5, 80° C.; (e) 1. 50% TFA/DCM, 2. LiOH, THF, r.t., 3. Amberlite IR-120 (H⁺).

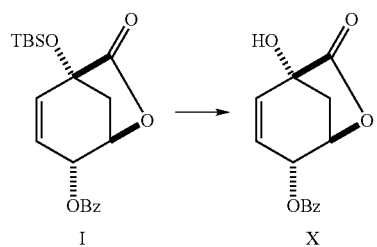

Preparation of (1R,3R,4R)-4-benzyloxy-1-hydroxycyclohex-5-ene-1,3-carbolactone (X). Tetrabutylammonium fluoride (6.4 mL, 6.36 mmol, 1.0 M commercial solution in THF) was added to a solution of compound 1 (2.16 g, 5.78 mmol) in 80 mL of dry THF under an argon atmosphere and at 0° C. After stirring for 30 minutes, it was acidulated with 10% HCl (20 mL) and the organic phase was extracted with dichloromethane (3×). The pooled organic phase was dried (Na₂SO₄ anh.), filtered and concentrated under reduced pressure. The obtained residue was purified by means of flash chromatography in silica gel (75% diethyl ether/hexanes) and recrystallized from hexanes to give 1.38 g of alcohol X in a white microcrystalline form (92%). [α]$^{25}_D$ –103° (c 0.6 in CHCl₃); M.P. 104-105° C. (hexanes); ¹H-NMR (250 MHz, CDCl₃, δ) 8.03 (dd, 2H, J 8.5 and 1.4), 7.60 (m, 1H), 7.46 (t, 1H, J 7.5), 6.30 (d, 1H, J 9.7), 5.88 (ddd, 1H, J 9.7, 3.3 and 1.1), 5.54 (t, 1H, J 3.0), 4.90 (m, 1H), 3.79 (broad s, 1H), 2.55 (ddd, 1H J 11.7, 5.2 and 1.7) and 2.49 (d, 1H J 11.7); ¹³C-NMR (63 MHz, CDCl₃, δ) 177.1, 165.2, 138.6, 133.7, 129.8, 128.9, 128.6, 124.2, 74.3, 73.3, 66.1 and 37.2; IR (KBr)/cm⁻¹ 3478, 1775 and 1722; EM-IQ⁺ (m/z) 261 (MH⁺); HRMS calculated for C₁₄H₁₃O₅ (MH⁺): 261.0763, 261.0755 found. Analysis calculated for C₁₄H₁₂O₅: C, 64.60; H, 4.65. Found: C, 64.60; H, 4.65.

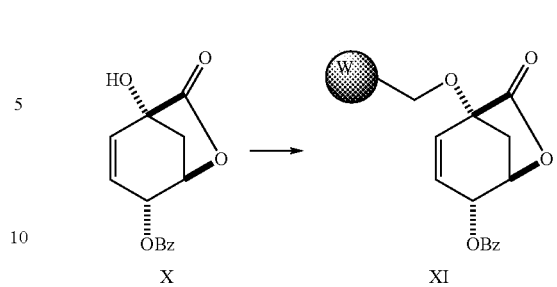

Preparation of Resin XI. Sodium hydride (264 mg, 6.60 mmol, 60% commercial suspension in mineral oil) was added to a solution of alcohol X (1.43 g, 5.48 mmol) in dry DMF (25 mL) at 0° C. and under an argon atmosphere. After 30 minutes, the resulting suspension was added by means of a cannula to a suspension of BromoWang polystyrene resin (1.4 g, ~1.6 mmol/g, ~2.24 mmol) in dry DMF (16 mL) at 0° C. and under an inert atmosphere. Then 15-crown-5 ether (60 μL, 0.32 mmol) was added and the resulting suspension was gently stirred at said temperature for 30 minutes and heated at 80° C. for 48 hours. The obtained resin was filtered and washed with DMF (3×20 mL), (3:1) DMF/water (3×10 mL), THF (3×10 mL) and dry dichloromethane (2×10 mL) to give 1.4 g of resin XI in brown granule form. IR (gel/cm⁻¹) 1794, 1718 and 1611; ¹³C-NMR (gel, 63 MHz, CDCL₃, δ) 137.0, 133.6, 129.5, 114.6, 73.6, 70.0, 67.5, 40.4 and 34.0.

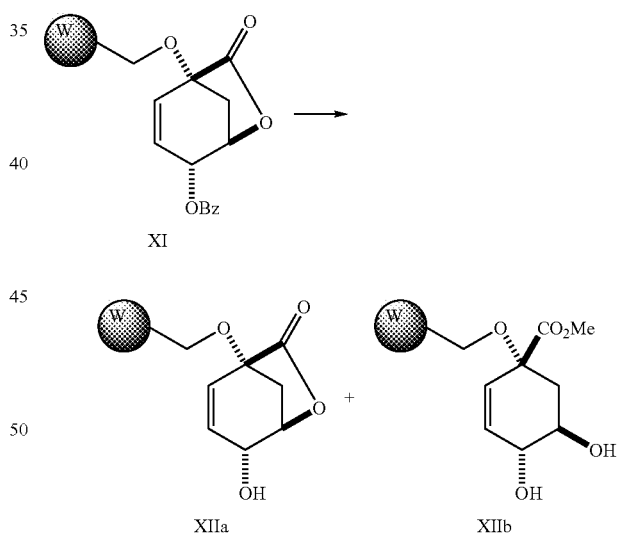

Preparation of Resin XII. A solution of potassium cyanide (136 mg, 2.09 mmol) in methanol (2 mL) was added to a solution of resin XI (1.1 g, ~1.3 mmol) in dry THF (6 mL). The resulting solution was bubbled with argon for 2 hours at room temperature. The resin was filtered and washed with THF (3×15 mL), methanol (3×15 mL), THF (3×15 mL) and dry dichloromethane (2×10 mL). ~1 g of resin XII was obtained in brown granule form. IR (gel/cm⁻¹) 3392, 1792, 1732 and 1604; ¹³C-NMR (gel, 63 MHz, CDCL₃, δ) 129.6, 114.6, 70.2, 67.4, 53.4 and 40.4.

The data of some compounds obtained using the processes hereinbefore mentioned are indicated below:

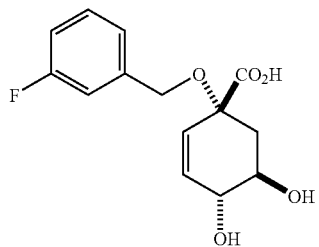

XIVa (1R,3R,4R)-1-(3'-fluorobenzyloxy)-3,4-dihydroxycyclohex-5-ene-1-carboxylic acid (XIVa). $[\alpha]^{25}_D$+11° (c 0.6 in $H_2O$); $^{19}$F-NMR (282 MHz, $D_2O$, δ) 111.8 (dt, 1F, J 9.6 and 5.6); $^1$H-NMR (250 MHz, $D_2O$, δ) 7.61 (m, 1H), 7.43-7.26 (m, 3H), 6.23 (d, 1H, J 10.1), 6.14 (dd, 1H, J 10.1 and 1.8), 4.72 (s, 2H), 4.31 (dt, 1H, J 8.2 and 1.7), 4.08 (ddd, 1H, J 12.2, 3.7 and 8.2), 2.44 (ddd, 1H, J 13.6, 3.0 and 1.1) and 2.19 (dd, 1H, J 13.6 and 12.2); $^{13}$C-NMR (63 MHz, $D_2O$, δ) 175.2, 162.9 (J 242), 140.6 (J 7), 134.6, 130.6 (J 8), 127.2, 124.5 (J 3), 115.4 (J 21), 115.1 (J 21), 80.0, 72.7, 69.6, 67.1 and 38.2; IR (KBr)/cm$^{-1}$ 3400, 1716 and 1592; EM-IQ$^+$ (m/z) 265 (MH$^+$—$H_2O$); HRMS calculated for $C_{14}H_{14}O_4F$ (MH$^+$): 265.0876, 265.0870 found.

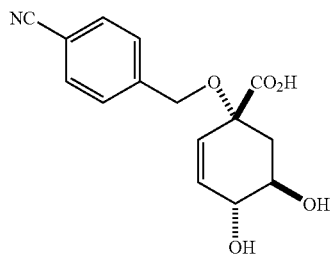

XIVb (1R,3R,4R)-3,4-dihydroxy-1-(4'-cyano)benzyloxycyclohex-5-ene-1-carboxylic acid (XIVb). M.P. 81-82° C.; $[\alpha]^{25}_D$+18° (c 0.6 in $CH_3OH$); $^1$H-NMR (250 MHz, $CD_3OD$, δ) 7.66 (d, 2H, J 8.3), 7.55 (d, 2H, J 8.3), 6.01 (d, 1H, J 10.1), 5.87 (dd, 1H, J 10.1 and 2.0), 4.64 (d, 1H, J 12.3), 4.56 (d, 1H, J 12.3), 3.98 (dt, 1H, J 7.8, 2.0 and 1.8), 3.86 (ddd, 1H, J 7.8, 11.5 and 3.6), 2.26 (ddd, 1H, J 13.3, 2.2 and 3.6) and 1.98 (dd, 1H, J 11.5 and 13.3); $^{13}$C-NMR (63 MHz, $CD_3OD$, δ) 177.2, 146.4, 135.7, 133.1, 129.3, 128.3, 119.8, 111.9, 80.8, 74.1, 70.9, 67.1 and 39.7; IR (KBr)/cm$^{-1}$ 3410, 2232 and 1716; EM-IQ$^+$ (m/z) 272 (MH$^+$—$H_2O$); HRMS calculated for $C_{15}H_{14}NO_4$ (MH$^+$): 272.0923, 272.0930 found.

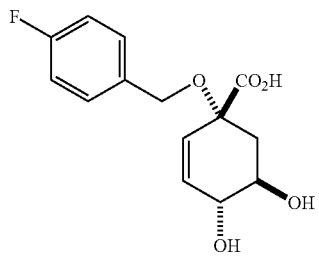

XIVc (1R,3R,4R)-1-(4'-fluorobenzyloxy)-3,4-dihydroxycyclohex-5-ene-1-carboxylic acid (XIVc). $[\alpha]^{25}_D$+9° (c 1.0 in $H_2O$); $^{19}$F-NMR (282 MHz, $D_2O$, δ) 112.6 (tt, 1F, J 9.1 and 5.2); $^1$H-NMR (250 MHz, $D_2O$, δ) 7.32 (dd, 2H, J 7.7 and 5.7), 7.04 (t, 2H, J 8.7), 5.91 (m, 2H), 4.40 (s, 2H), 4.03 (dd, 1H, J 8.2 and 1.2), 3.78 (ddd, 1H, J 11.6, 8.2 and 3.45), 2.15 (dd, 1H, J 13.6 and 3.45) and 1.90 (t, 1H, J 13.6 and 11.6); $^{13}$C-NMR (63 MHz, $D_2O$, δ) 177.8, 162.7 (J 242), 134.8, 133.8, 131.1 (J 8), 127.0, 115.6 (J 21), 80.3, 72.7, 69.6, 67.2 and 38.0; IR (KBr)/cm$^{-1}$ 3420, 1716 and 1605; EM-IQ$^+$ (m/z) 265 (MH$^+$—$H_2O$); HRMS calculated for $C_{14}H_{14}O_4F$ (MH$^+$): 265.0876, 263.0880 found.

The invention claimed is:
1. Compounds of formula (1):

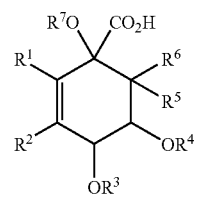

(1)

wherein
$R^1$ is selected from the group consisting of:
   a hydrogen atom;
   an alkyloxy group;
   an aromatic group;
   a benzyloxy group;
   a linear or branched alkyl group with 1-10 carbon atoms;
   an alkenyl group with 2 to 10 carbon atoms;
   an alkynyl group with 3 to 10 carbon atoms;
   a cycloalkyl group with 3 to 6 carbon atoms;
   a cycloalkenyl group with 4 to 6 carbon atoms; and
   a bicycloalkyl with 7 to 10 carbon atoms;
$R^2$ is selected from the group consisting of:
   an alkyloxy group;
   an aromatic group;
   a benzyloxy group;
   a linear or branched alkyl group with 1-10 carbon atoms;
   an alkenyl group with 2 to 10 carbon atoms;
   an alkynyl group with 3 to 10 carbon atoms;
   a cycloalkyl group with 3 to 6 carbon atoms;
   a cycloalkenyl group with 4 to 6 carbon atoms; and
   a bicycloalkyl with 7 to 10 carbon atoms;
$R^3$, $R^4$, and $R^7$ are selected from the group consisting of a hydrogen atom or an alkyl group with $C_{1-10}$ chain; and
$R^5$, $R^6$ are hydrogen atoms.

2. Compounds of formula (1) according to claim 1, wherein at least one of $R^1$ and $R^2$ is a benzyloxy group, comprising an aromatic ring substituted by one or several identical or different radicals chosen from halogen, nitro, azido, amino, phosphate, carboxy, cyano, amide, thiol, thioester, thioether, guanidinium, alcohol, alkoxy or alkyl groups with $C_{1-10}$ chain.

3. Compounds of formula (1) according to claim 1, wherein at least one of $R^1$ and $R^2$ is a linear or branched alkyl group with 1-10 carbon atoms, an alkenyl group with 2 to 10 carbon atoms, an alkynyl group with 3 to 10 carbon atoms, a cycloalkyl group with 3 to 6 carbon atoms, a cycloalkenyl group with 4 to 6 carbon atoms or a bicycloalkyl with 7 to 10 carbon atoms, substituted by:
   halogen atom;
   hydroxy;
   amino;
   thiol;
   azido;

nitro;
piperidinyl;
morpholinyl;
indole;
furan;
piperazinyl-1;
cycloalkyl with 3 to 6 carbon atoms;
cycloalkenyl with 4 to 6 carbon atoms;
cyano;
alkoxycarbonyl;
halogen;
amino or amide wherein the alkyl part of which comprises 1 to 4 carbon atoms; or
phenyl.

4. Compounds according to claim 3, wherein said piperazinyl-1 is substituted at position 4 by an alkyl comprising 1 to 4 carbon atoms.

5. Compounds according to claim 3, wherein said piperazinyl-1 is substituted at position 4 by a phenylalkyl, the alkyl part of which comprises 1 to 4 carbon atoms.

6. Compounds according to claim 3, wherein said phenyl group is substituted by a radical selected from the group consisting of an alkyl with 1 to 4 carbon atoms, an alkoxy with 1 to 4 carbon atoms, an halogen, a nitro, an azido, a phosphate, an amino, a cyano, an amide, a thiol, a thioester, a thioether, a guanidinium or an alcohol group, a saturated or unsaturated nitrogenous heterocyclic radical containing 1 to 4 carbon atoms, and a saturated or unsaturated nitrogenous heterocyclic radical containing 5 or 6 members.

7. Compounds according to claim 6, wherein said alkyl group with 1 to 4 carbon atoms is halogenated.

8. Compounds according to claim 6, wherein said saturated or unsaturated nitrogenous heterocyclic radical containing 5 or 6 members is substituted by one or several alkyl radicals with 1 to 4 carbon atoms.

9. Compounds according to claim 3, wherein said cycloalkyl, cycloalkenyl or bicycloalkyl radical is substituted by one or several alkyl radicals with 1 to 4 carbon atoms.

10. Compounds of formula (1) according to claim 1, wherein said alkyl group with a $C_{1-10}$ chain of $R^3$, $R^4$ and $R^7$ is substituted by a phenyl group.

11. Compounds according to claim 10, wherein said phenyl group is substituted by one or several identical or different radicals, selected from the group consisting of:
an alkyl with 1 to 4 carbon atoms;
an alkoxy with 1 to 4 carbon atoms;
a halogen group;
a nitro group;
an azido group;
a phosphate group;
an amino group;
a cyano group;
an amide group;
a thiol group;
a thioester group;
a guanidinium group;
an alcohol group;
a saturated or unsaturated nitrogenous heterocyclic radical containing 1 to 4 carbon atoms; and
a saturated or unsaturated nitrogenous heterocyclic radical containing 5 or 6 members.

12. Compounds according to claim 11, wherein said alkyl with 1 to 4 carbon atoms is halogenated.

13. Compounds according to claim 11, wherein said saturated or unsaturated nitrogenous heterocyclic radical containing 5 or 6 members is substituted by one or several alkyl radicals with 1 to 4 carbon atoms.

* * * * *